(12) United States Patent
Berme et al.

(10) Patent No.: US 6,389,883 B1
(45) Date of Patent: May 21, 2002

(54) DEVICE, SYSTEM, AND METHOD FOR MEASUREMENT OF BALANCE, STABILITY, AND TREMOR

(75) Inventors: Necip Berme, Worthington; Douglas R. Morr, Westerville, both of OH (US)

(73) Assignee: Bertec Corporation, Worthington, OH (US)

( * ) Notice: Subject to any disclaimer, the term of this patent is extended or adjusted under 35 U.S.C. 154(b) by 0 days.

(21) Appl. No.: 09/420,854

(22) Filed: Oct. 19, 1999

(51) Int. Cl.[7] ................................................ G01M 1/00
(52) U.S. Cl. ...................................................... 73/65.01
(58) Field of Search ......................... 73/65.01, 862.042, 73/862.045, 794, 862.627, 862.044; 600/595

(56) References Cited

U.S. PATENT DOCUMENTS

| | | |
|---|---|---|
| 4,493,220 A | 1/1985 | Carignan |
| 4,805,637 A | 2/1989 | Walthert |
| 5,022,475 A | 6/1991 | Sato |
| 5,052,406 A | 10/1991 | Nashner |
| 5,154,247 A | 10/1992 | Nishimura |
| 5,230,252 A | 7/1993 | O'Brien |
| 5,269,318 A | 12/1993 | Nashner |
| 5,303,715 A | 4/1994 | Nashner |
| 5,400,661 A | 3/1995 | Cook |
| 5,474,087 A | 12/1995 | Nashner |
| 5,476,103 A * | 12/1995 | Nashner ..................... 128/782 |
| 5,551,445 A | 9/1996 | Nashner |
| 5,570,301 A | 10/1996 | Rurrus |
| 5,623,944 A | 4/1997 | Nashner |
| 5,627,327 A | 5/1997 | Zanakis |
| 5,697,791 A | 12/1997 | Nashner |
| 5,723,792 A | 3/1998 | Miyazaki |
| 5,814,740 A * | 9/1998 | Cook et al. ............ 73/862.641 |
| 5,821,432 A * | 10/1998 | Sidler et al. ........... 73/862.042 |
| 5,889,214 A | 3/1999 | Kang |
| 5,913,242 A | 6/1999 | Stussi |
| 5,919,149 A * | 7/1999 | Allum ........................ 600/595 |

* cited by examiner

*Primary Examiner*—Benjamin R. Fuller
*Assistant Examiner*—Octavia Davis
(74) *Attorney, Agent, or Firm*—Francis T. Kremblas, Jr.

(57) ABSTRACT

This invention is a system to analyze the balance, stability, and tremor of a load or subject by measuring forces and calculating the center of pressure, as well as being capable of measuring all forces and moments. The plate (or platform) component of the system houses the measurement, amplification, and transmission technology. The forces and moments are measured by strain gages which are geometrically attached to specially machined beams inside the plate. The plate has a low profile for ease of stepping on and off, is light weight for portability, and is adjustable to compensate for unlevel surfaces. The data acquisition component of the system allows the user to analyze, interact with, and observe the measurement data. One version of the invention utilizes a compressible pad which can be placed on the plate to perturb the load or subject without interfering with the plate's capabilities. Another version of the invention incorporates a specially designed support structure and harness to ensure subject safety and allow for greater balance and stability testing ranges without interfering with the plate's capabilities.

3 Claims, 12 Drawing Sheets

DEVICE, SYSTEM, AND METHOD FOR MEASUREMENT OF BALANCE, STABILITY, AND TREMOR

BACKGROUND OF THE INVENTION

Force measuring platforms, which are primarily designed to measure the location of the center of pressure, and mainly used in balance assessment and related fields, are generally known as balance plates. As a typical subject tested on a balance plate has a balance disorder or a potential balance problem, it is important that subjects can easily step on and off a balance plate. Therefore, it is very desirable that balance plates have as low a profile as possible. A further desirable characteristic of a balance plate is its portability. Therefore, it should be light weight, and house the associated electronics within the plate itself.

The measurement technology of the prior art does not accomplish the above desirable characteristics. The prior designs utilize pin-wheel measurement devices with cross-beams inside the wheel, or four or more load cells to measure forces, or piezoelectric technology, or elaborate systems of machined beams and plates, or the combination of measuring plates, or utilizing a platform with rockers underneath. Most are incapable of measuring both forces and moments. These past designs were bulky and cumbersome making them difficult to get on and off of, as well as difficult to transport.

BRIEF SUMMARY OF THE INVENTION

The purpose of the disclosed invention is to provide the means for analyzing and measuring the balance, functional capability, and stability of a subject or load. The present invention is directed to a balance analysis system that satisfies the measurement capabilities, low profile, and portability needs identified in the BACKGROUND section above.

Figure 1:
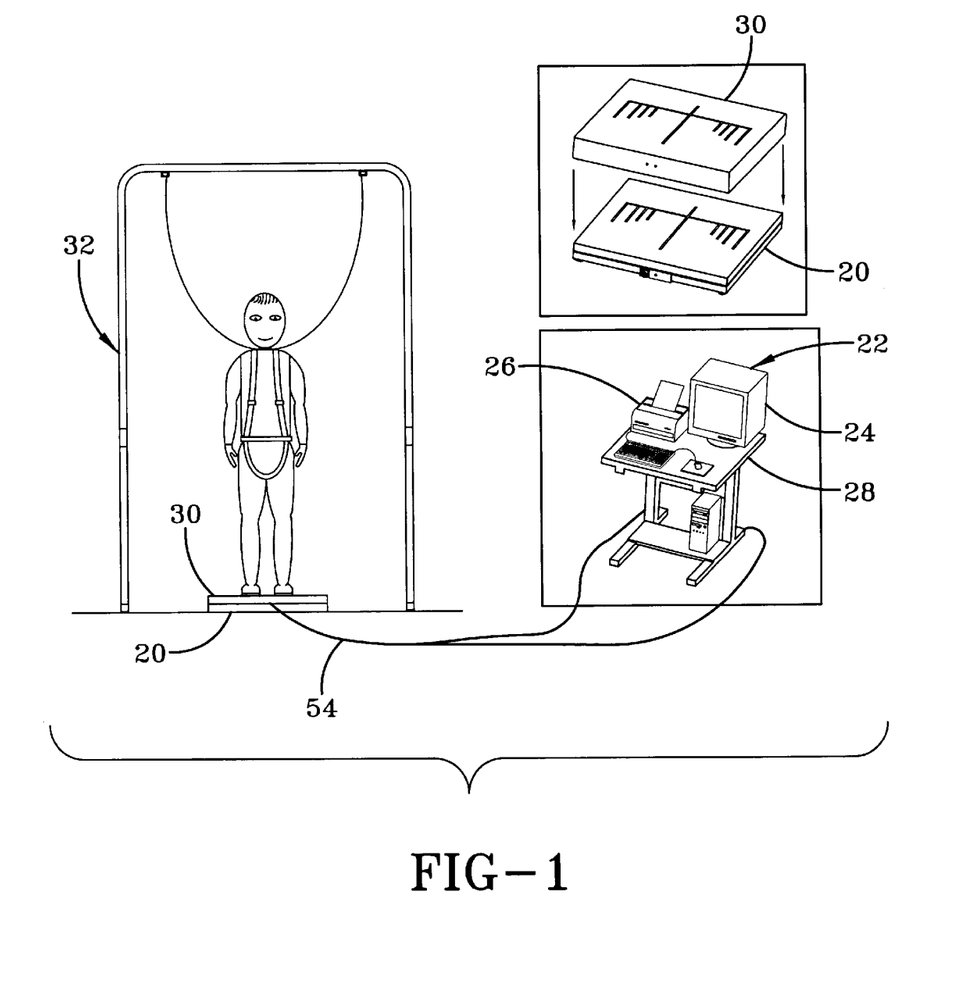
FIG. 1 is a perspective view of the first preferred embodiment of the invention, comprised of: a subject in a harness attached to a support structure while standing on a plate connected to a data collection device by a "Y" cable, with an exploded view of placing a pad on a plate.

This object is accomplished by disclosing a balance plate (or "platform") system FIG. 1 capable of measuring all force and moment components and calculating the location of the center of pressure of the subject or load. Other versions of the invention measure the force components at each corner of the plate and calculate the center of pressure. Internally, the plate is comprised of two or more beams FIG. 3 and FIG. 3A with two or more strain gages geometrically affixed to each beam FIG. 4 allowing for the measurement of up to six force and moment components. The beams and gages are enclosed in a light-weight, portable, and level-adjustable housing structure which has a low profile for ease of load placement and accessibility by a human or animal subject for stepping onto and off of the plate FIG. 2. Within the plate is the necessary technology for data collection and transmission; including, signal amplification device(s) and signal transmission device(s) FIG. 5. For analysis, display, and interpretation of the data collected by the plate, a data collection device and the necessary hardware and software therefore are employed FIG. 1; including, data acquisition device(s) (e.g., computers, desk-top or lap-top versions utilizing monitors and printers, and data acquisition cards), as well as computer program(s) for analysis, display, interpretation of the data, and user interaction with the system.

Figure 9:
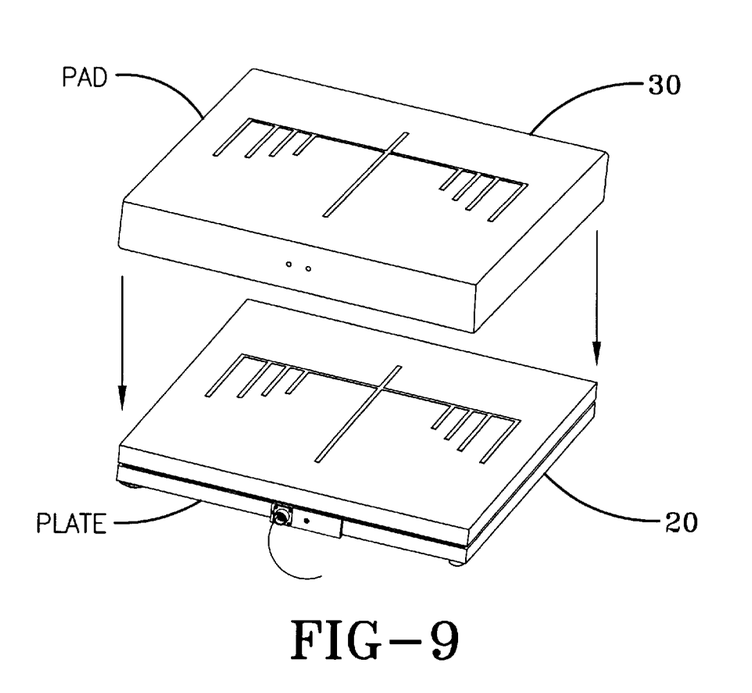
FIG. 9 is a perspective view of perturbance pad placement on a plate.
Figure 10:
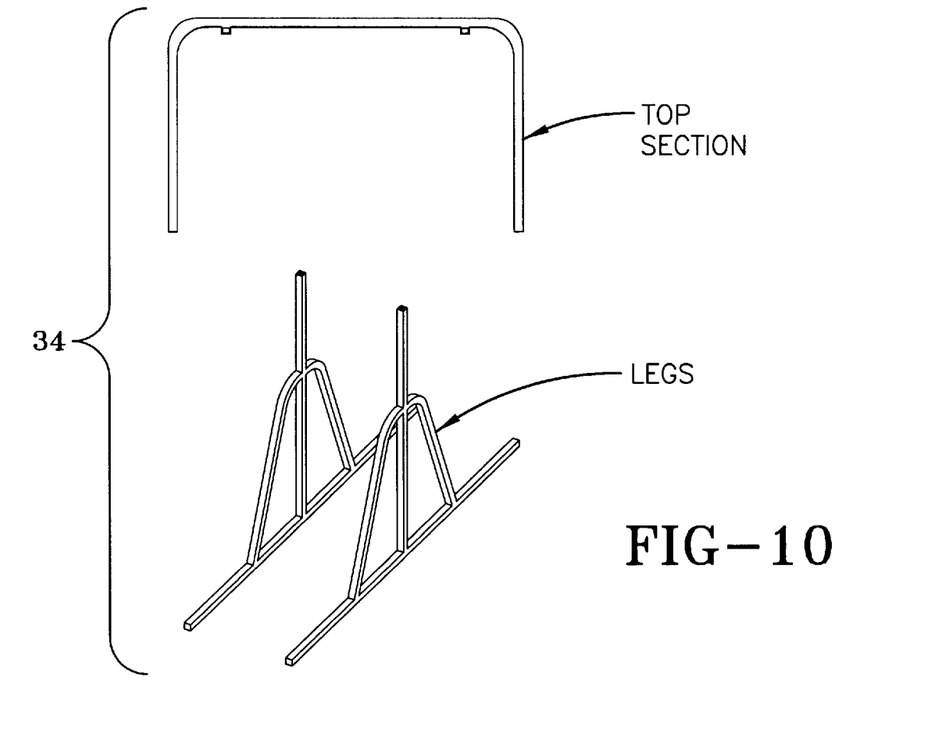
FIG. 10 is a view of the elements of a support structure.
Figure 11:
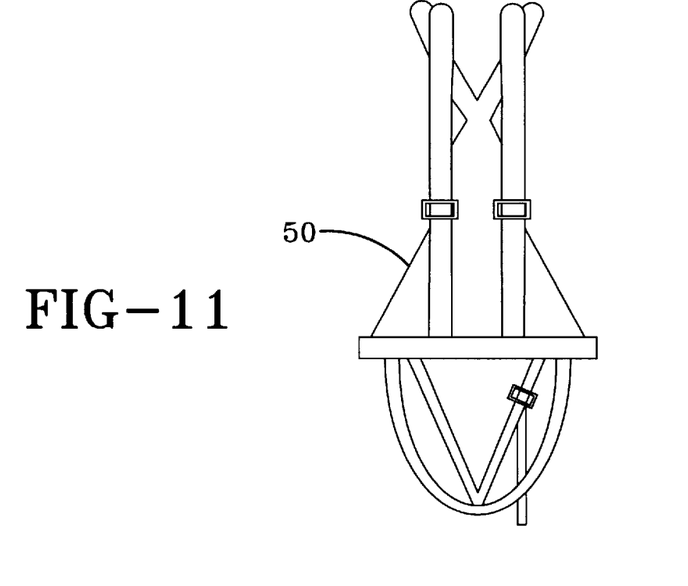
FIG. 11 is a view of the elements of a harness.

When used to analyze a subject, an optional support structure FIG. 10 with an adjustable harness FIG. 11 can be employed to ensure safety, and allow for a greater range of measurement during sway and perturbance tests. The perturbance tests can be performed with a pad made of compressible material as disclosed herein FIG. 9.

This device and system has multiple applications in the biomechanical and medical fields; including, but not limited to, the measuring and testing of a subject's balance, coordination, gait, movement, posture, stability and instability, and sway. Generally, versions of this invention will be used to test for the existence of balance problems in a subject or the likelihood of a balance problem, as well as the magnitude of the problem, and aid in the determination of the cause; whether the cause is inner ear, muscular, neurological, ocular, skeletal related, or otherwise. The disclosed plates are sensitive enough to measure the tremor (s) in patients, and then using an algorithm the data collected is viewed in the frequency domain to reveal the potential ability to decipher such things as the stage of Multiple Sclerosis, and the efficacy of drug dosages for Parkinson's disease.

Because up to six degrees of freedom can be measured, there are many applications beyond the general-clinical measuring and testing. For example, this device and system can measure and test for the effects and impairments of drugs (e.g., alcohol) on a subject's capability to function. Likewise, this system can be employed to measure an athlete's functional capability prior to, during, or after activity, or to measure the subject's capability to return to the activity after an injury.

Therefore, the presently disclosed balance analysis system improves upon the prior art and provides for the means of measuring and testing a subject's balance neither contemplated nor demonstrated by the prior art.

BRIEF DESCRIPTION OF THE SEVERAL VIEWS OF THE DRAWINGS

FIG. 1 is for the Official Gazette.

DETAILED DESCRIPTION OF THE INVENTION

The invention disclosed herein is a system for the measurement of a subject's or load's center of pressure and tremor. The purpose of the disclosed invention is to provide the means for analyzing and measuring the balance, functional capability, and stability of a subject or load. The present invention is directed to a balance analysis system that satisfies the measurement capabilities, low profile, and portability needs identified in the BACKGROUND section above.

1. Preferred Embodiments

One preferred embodiment is where all elements of the balance analysis system are combined FIG. 1. Fully assembled, this version of the system is comprised of: a balance plate (or "platform") 20 which houses the measuring, amplification, and transmission technology; connection cables or a wireless transmission device for data transmission and a power cord or internal power; a data collection device indicated generally at 22 for analysis and interpretation, including a monitor 24, printer 26, and cart or desk 28; a compressible pad 30 equal in length and width to the plate for balance perturbance testing; and a support structure with a harness system attached thereto, indicated generally at 32, providing safety for the subject.

Figure 2:
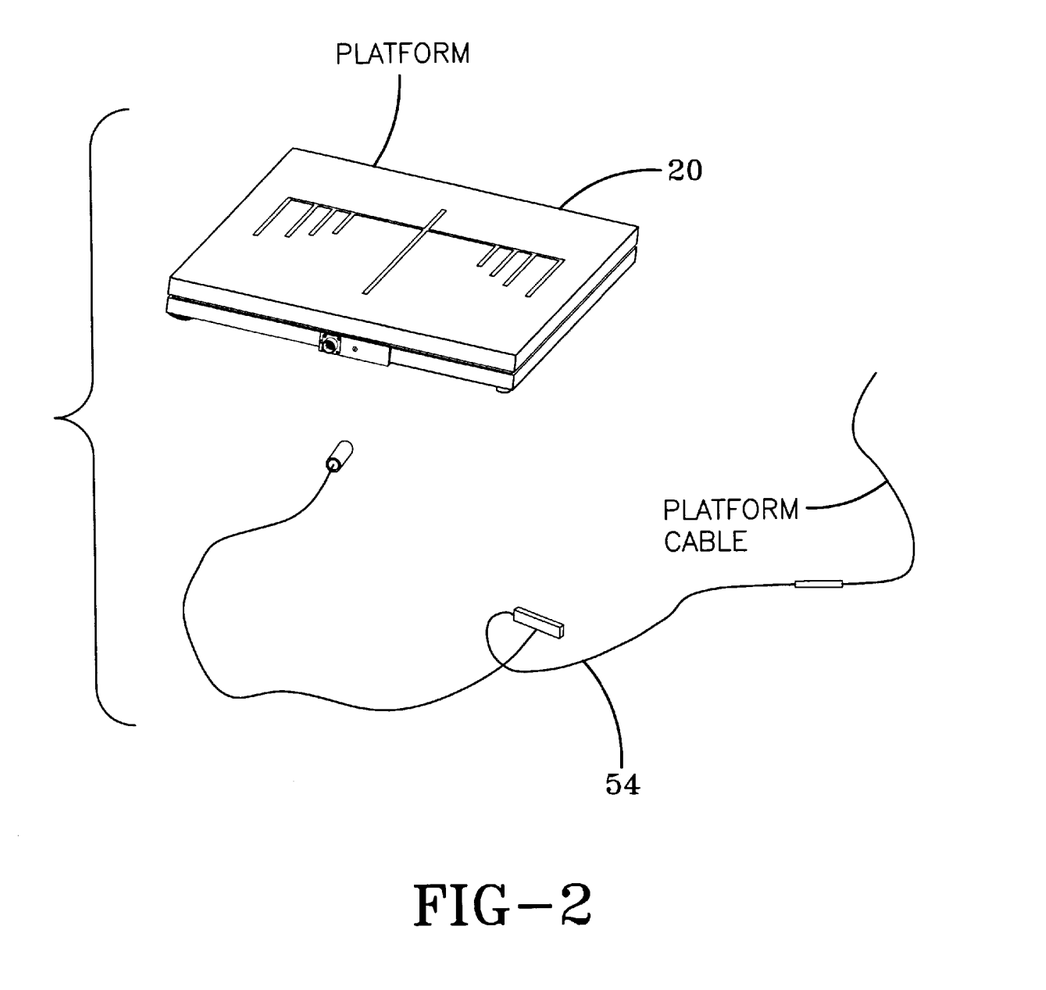
FIG. 2 is a perspective view of the plate and "Y" cable.
Figure 3:
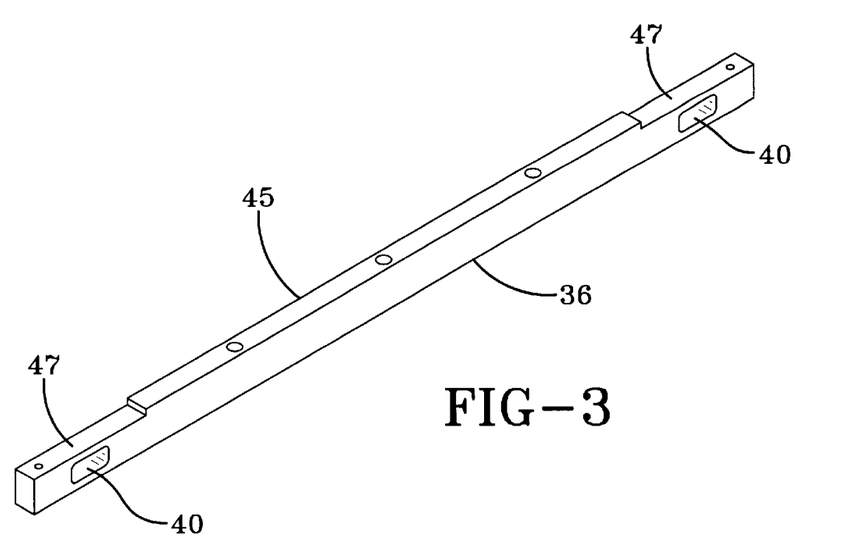
FIG. 3 is a perspective view of a beam capable of measuring force components.
Figure 3A:
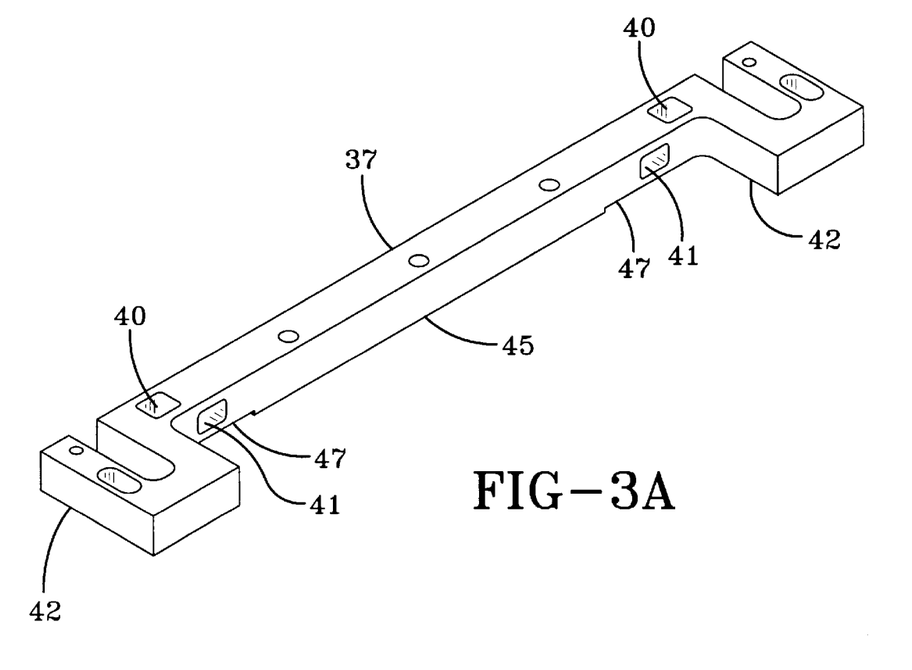
FIG. 3A is a perspective view of a beam capable of measuring up to six force and moment components.
Figure 4A:
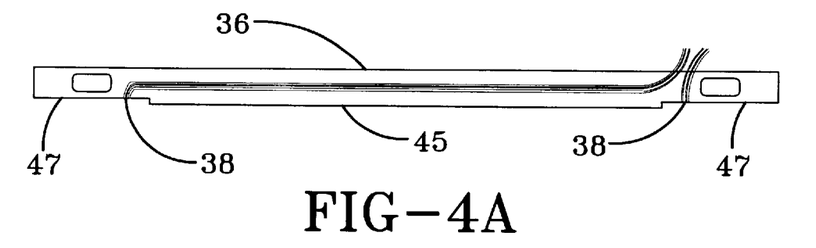
FIG. 4 are side and top views of a beam with strain gages and wiring.
Figure 4B:
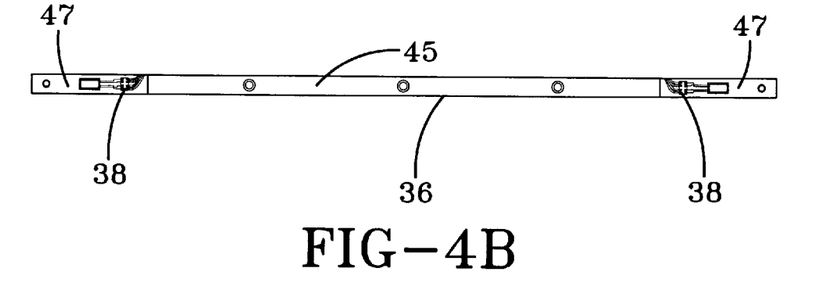
Figure 5:
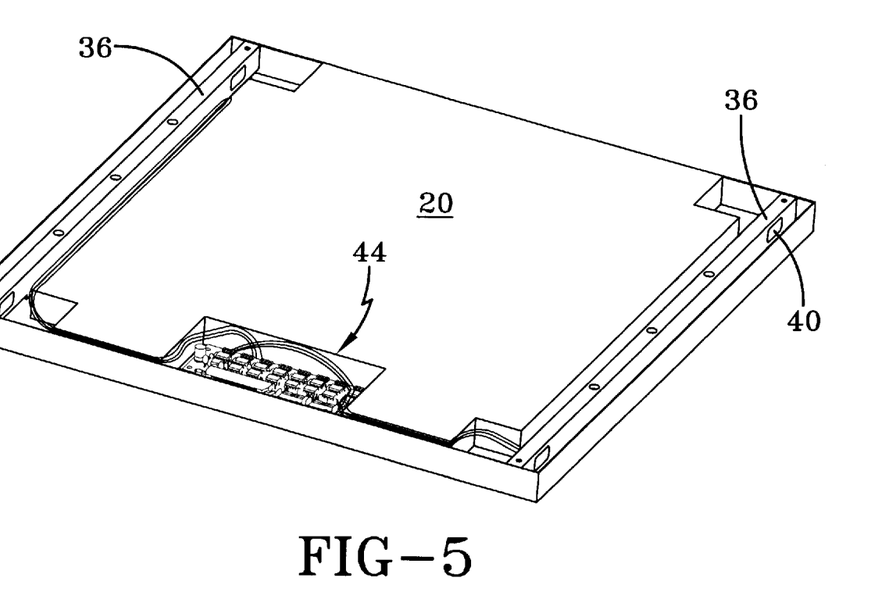
FIG. 5 is a perspective view of the technology inside a plate.
Figure 6:
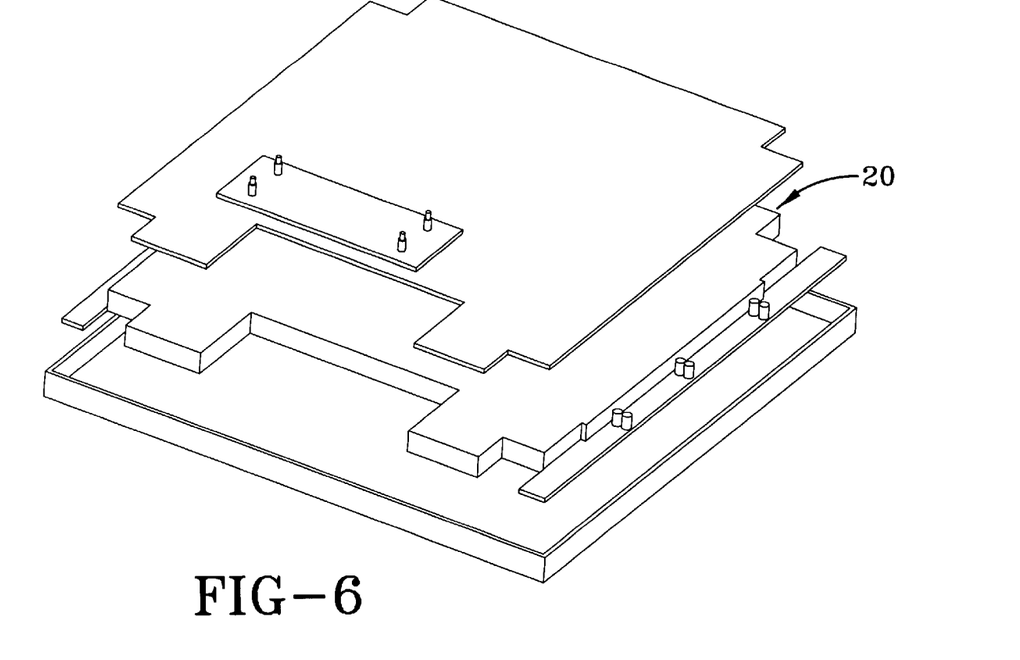
FIG. 6 is an exploded view of the construction material inside a plate.
Figure 7:
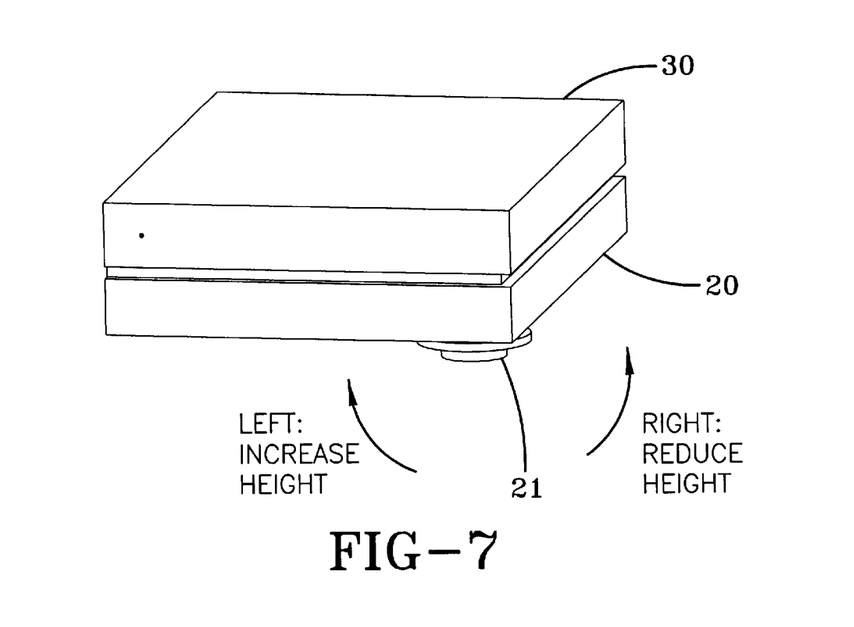
FIG. 7 is a perspective view of the level-adjustable foot on a plate.
Figure 8:
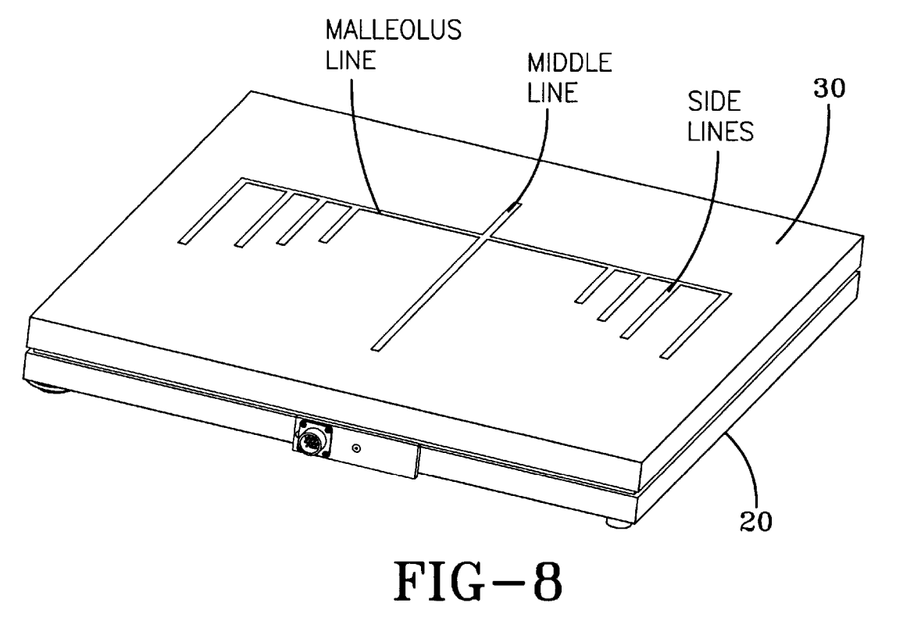
FIG. 8 is a perspective view and description of the markings on a plate.

The balance plate (or "platform") 20, FIG. 2, measures the center of pressure, along with the capability of measuring all force and moment components, by utilizing two or more parallel beams, such as 36 or 37 FIG. 3 and FIG. 3A, with two or more strain gages such as 38 attached to each beam, FIGS. 4-A and 4-B. Beams 36 and 37 include an upper and lower surface. The lower surface includes a central portion 45 and opposing end portions 47 disposed at different vertical levels relative to central portion 45. Central portion 45 will engage the substrate upon which the beam 36 or 37 rests with end portions 47 each raised above the substrate so as to form opposing cantilever end portions on each beam. At both ends of each beam 36 or 37 are specially machined holes 40, FIG. 3, or specially machined holes 40, 41 and "U" shaped ends 42, FIG. 3A, which allow for the measurement of the forces and moments. Strain gages 38 are attached to the beams and geometrically positioned to measure the desired force components, FIG. 4. The technology, indicated generally at 44, inside the plate structure 20 includes wiring for signal transmission and a signal amplification system, FIG. 5, and construction material for stability, FIG. 6. The plate 20 is light-weight and portable with an adjustable foot 21 to compensate for unleveled surfaces, FIG. 7. The plate 20 has a low profile, and being close to the ground allows for ease of stepping on and off the plate. Markings (e.g., lines) are made on the top surface of the plate, FIG. 8, for proper subject and load positioning.

In this preferred embodiment, a pad of compressible material 30 (e.g., a piece of foam) can be placed on the plate 20, FIG. 9, thus perturbing the subject's balance for greater analysis of the subject's coordination and stability. The pad 30 should be approximately the width and length of the plate 20 with markings on the pad, as are on the plate, for proper positioning of the pad onto the plate and proper positioning of the subject and load onto the pad 30, FIG. 9. The underside of the pad 30 is equipped with non-slip and non-abrasive material to prevent it from moving while on the plate and to prevent damage to the surface of the plate.

For transmission of the data and as a power supply, this embodiment employs a Y-cable 54 in FIG. 2 where there is only one connection to the plate, then the cable splits into a power supply cable and a data transmission cable. The single connection to the plate creates a simpler design, efficiency, and greater safety where test subjects will not have to be maneuvered around multiple obstacles. In other preferred embodiments, the plate can stand alone using a wireless transmission system and an internal power supply.

This preferred embodiment employs a data collection device 22 (e.g., a computer, desk-top or lap-top versions) comprised of a computer program for analyzing, compiling, displaying, and interpreting the data and a monitor for visual display of the data, the program's conclusions, and the display screens. This version of the invention enables the user to interact with the program by selecting displays, entering data regarding the subject, saving data, and producing printouts of the data and screens. An accompanying printer allows the user to reproduce the display screens and data in hard copy form. This embodiment can utilize either desk-top or lap-top computer systems.

Figure 12:
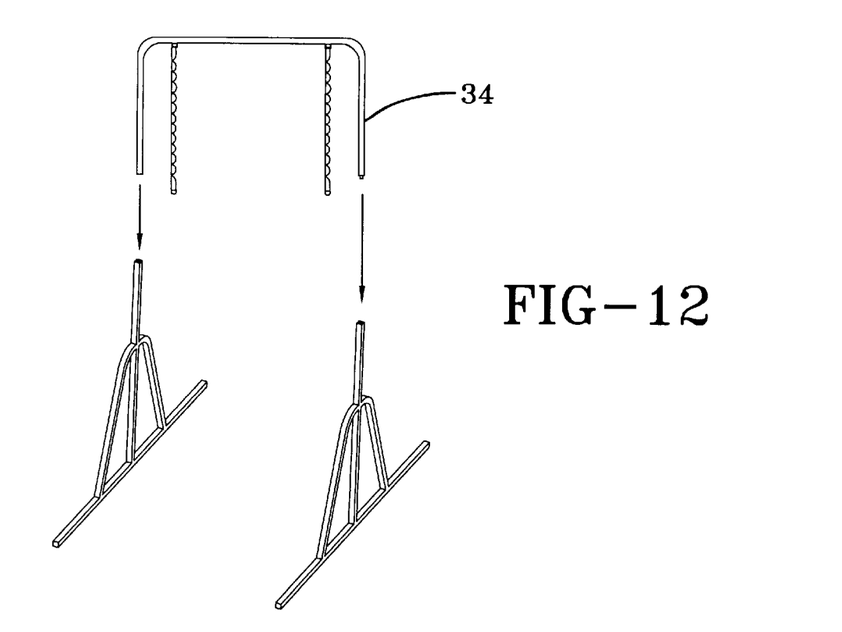
FIG. 12 is a perspective view of support structure assembly.
Figure 13:
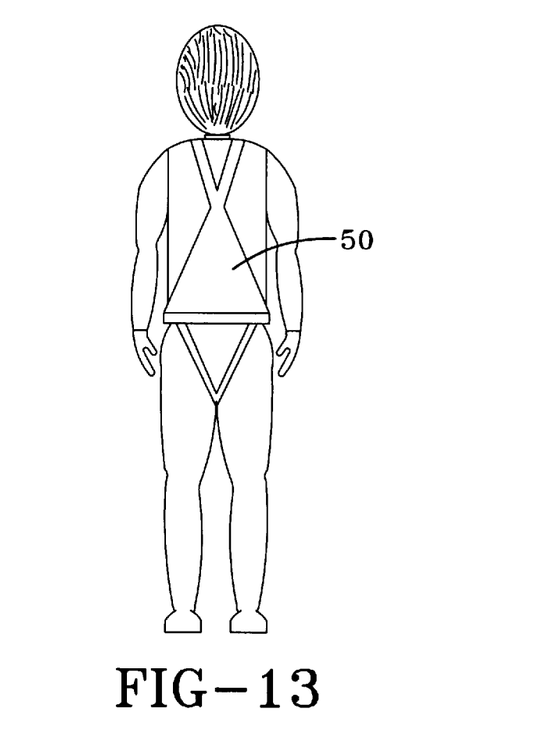
FIG. 13 is a front and rear view of a harness on a subject.
Figure 14:
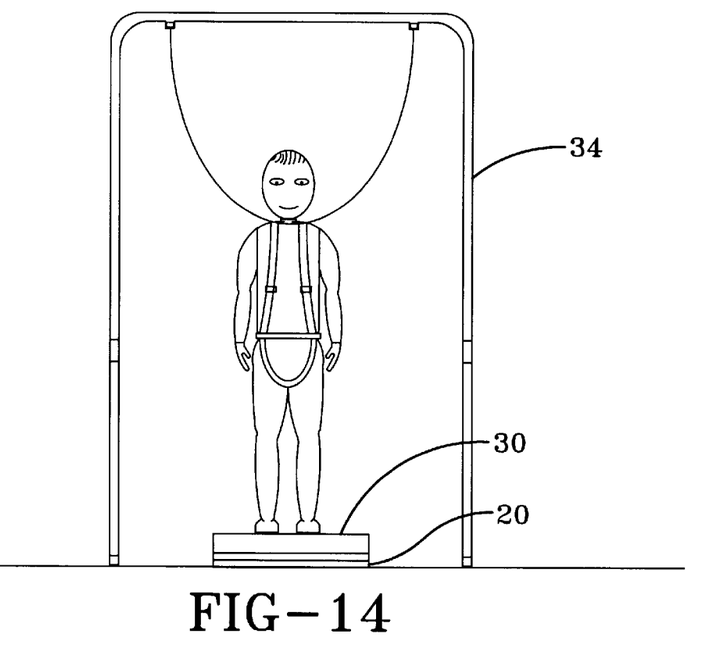
FIG. 14 is a front view of a subject on a perturbance pad utilizing the support structure and harness.

The final component of this preferred embodiment is the support structure 34, FIG. 10 and harness 50, FIG. 11. For efficient transport and ease of assembly, the support structure is comprised of multiple pieces, FIG. 10. The pieces are specially machined to allow for ease of assembly and stability once assembled. There is a "U" shaped top-section which fits onto the two leg-sections so that the top-section becomes an upside-down "U", FIG. 12. The top-section is machined so that the harness can be hung from it, FIG. 12. The two "T" shaped leg-sections sit perpendicular to the cross beam of the top-section to form an upside-down "T" with support struts vertical from the base of the leg-sections to the perpendicular bar of the leg-sections, FIG. 12. The structure forms an archway under which the plate is positioned and the subject can walk into or through, FIG. 1. A harness is attached to the support structure, then placed onto and around the subject, FIG. 13. The harness is adjustable for the analysis and comfort of various types of subjects, as well as strong to ensure safety and support of the subject. When attached to the support structure, the harness acts to provide security and stability to the subject for a wider range of balance testing, while still allowing for accurate measurement of the subject's balance. The structure and harness can be employed as shown in FIG. 14 or in FIG. 15 without the perturbance pad 30 on the plate 20. When the subject's safety and support are not issues, the support structure and harness are not needed. Accurate measurement of a subject's or load's balance can be taken with or without the structure and harness.

Figure 15:
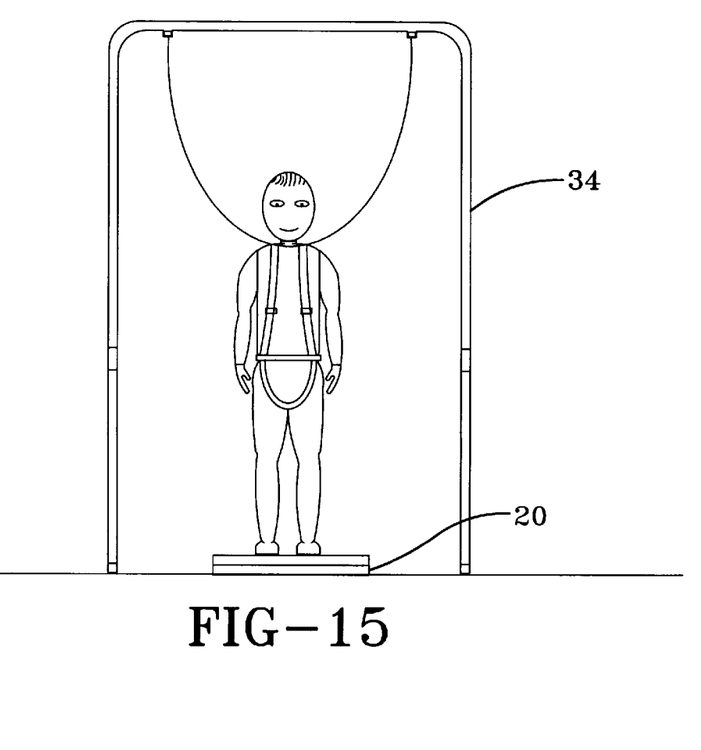
FIG. 15 is a front view a subject on a plate utilizing the support structure and harness.

Other preferred embodiments would comprise only the components from the above necessary to perform the desired measurement(s) or test(s). Therefore, a second preferred embodiment would be comprised of: the plate 20 shown in FIG. 2, transmission devices in FIG. 2, and a data acquisition device 22 (e.g., a desk-top or lap-top computer). This version can perform all the balance measuring tests where the subject's safety is not an issue. For example, athletic testing, drug testing, or clinical tests for balance, coordination, posture, or sway where the subject will not lean or sway outside safe ranges. If safety is an issue, then the support structure and harness as shown in FIG. 14 or FIG. 15 should be utilized to maximize the subject's security.

A third preferred embodiment, would add the perturbance pad 30 to the second preferred embodiment. The perturbance pad creates instability in the subject's balance. Thus, the tester can measure the subject's ability to regain and maintain balance. This version only requires the support structure and harness when the subject will be tested outside safe ranges or the subject's safety is at issue.

2. Applications

The capability of measuring all force and moment components or the force components to calculate the center of pressure, allows this system and its different versions to perform multiple kinds of measurements and testing, as well as having various applications. For example, there are three main methods of tests which can be performed to measure a subject's balance and ability to maintain his/her balance: Normal Stability, Perturbed Stability, and Limit of Stability.

Figure 16:
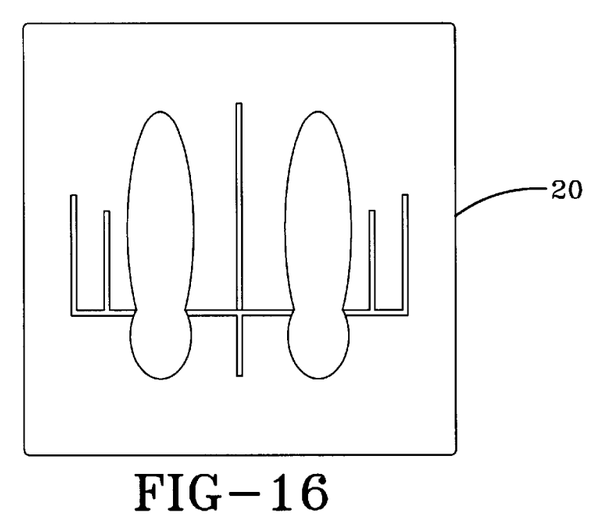
FIG. 16 is a top view exemplifying foot placement on a plate or perturbance pad.

The Normal Stability tests require the subject to stand still on the platform 20 in a comfortable position with the feet symmetrically apart, FIG. 16. The ability to maintain balance is evaluated in two conditions: first, with the subject's eyes open, and second, with his/her eyes closed. These results are compared with standard results obtained for a person the same height as the subject.

The Perturbed Stability tests require the subject to stand still on a soft surface. The equilibrium is perturbed by having a compressible cushion (the pad) 30 between the subject's feet and the platform, FIG. 14. The ability to maintain balance is again evaluated in two conditions: first, with the subject's eyes open, and second, with his/her eyes closed. These results are compared with standard results obtained for a person the same height as the subject.

Figure 17:
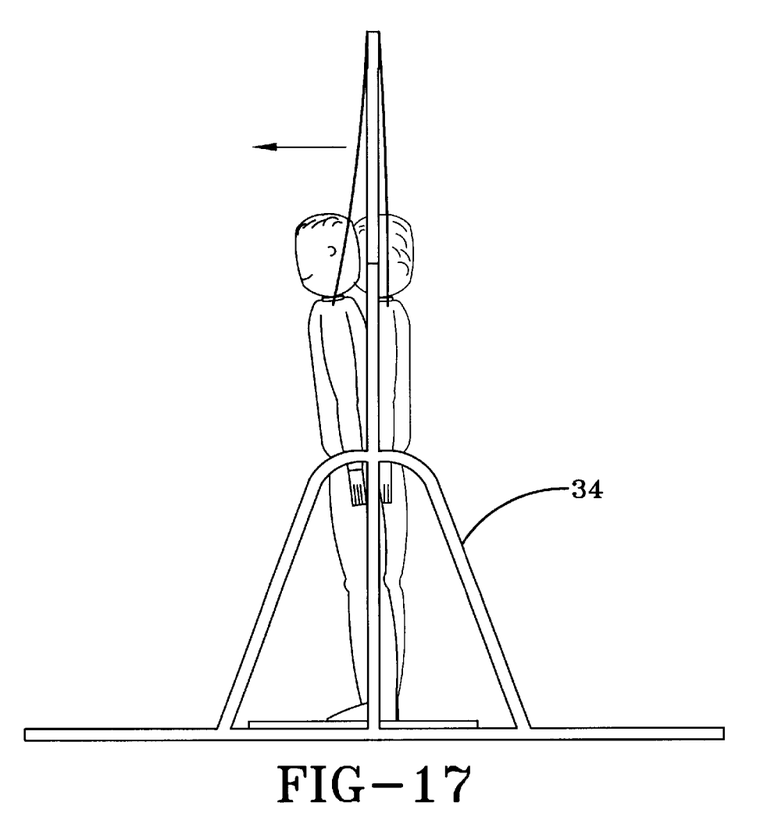
FIG. 17 is a side view of a subject leaning forward utilizing the support structure and harness.
Figure 18:
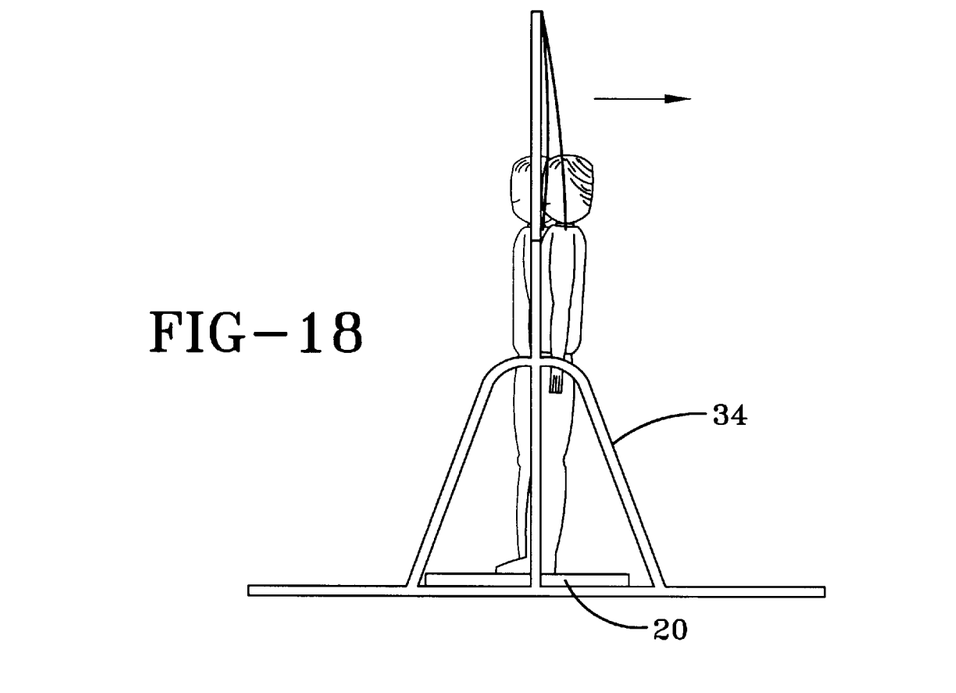
FIG. 18 is a side view of a subject leaning backward utilizing the support structure and harness.
Figure 19:
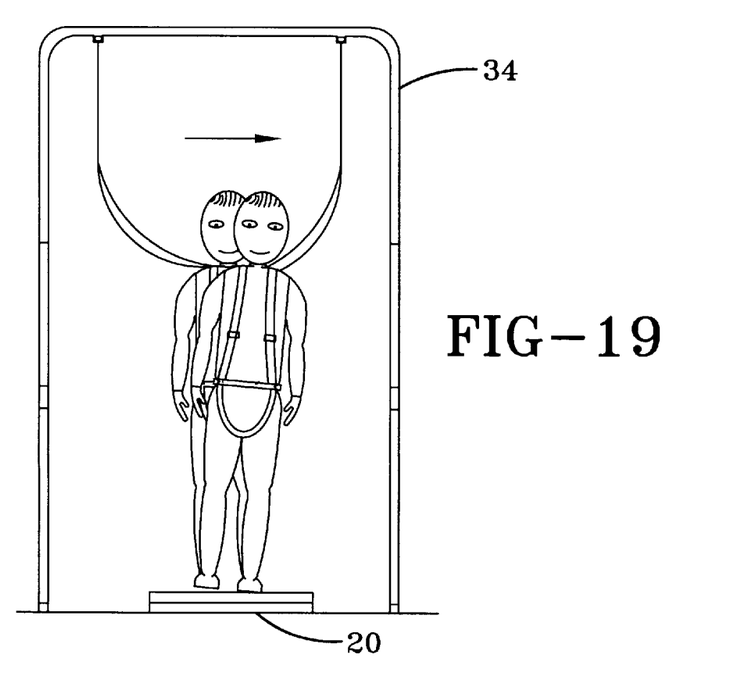
FIG. 19 is a front view of a subject leaning leftward utilizing the support structure and harness.
Figure 20:
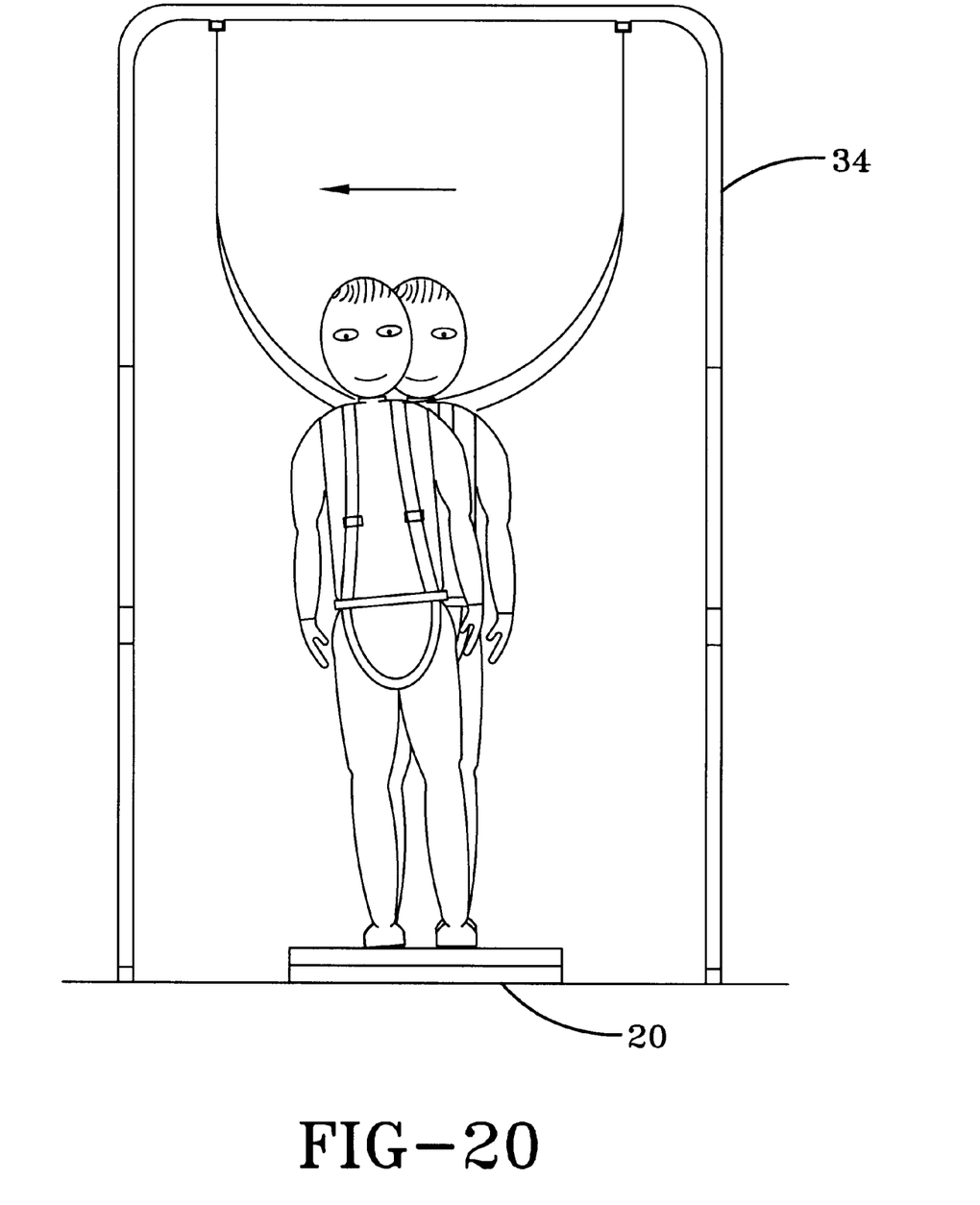
FIG. 20 is a front view of a subject leaning rightward utilizing the support structure and harness.

The Limit of Stability is evaluated through a series of four tests that require the subject to stand on the platform 20 in a comfortable position with the feet symmetrically apart, FIG. 16, and to lean in four different directions. The Limit of Stability is evaluated in the sagital and lateral directions: the subject is asked to lean forward, FIG. 17, backward, FIG. 18, leftward, FIG. 19, and rightward, FIG. 20, as far as possible without losing balance. For the subject's safety and to allow for a full range of measurements, the support structure 34 and harness 50 should be employed during the Limit of Stability tests. The Limit of Stability is compared with standard results obtained for a person the same height as the subject. A comparison between the subject's Limit of Stability and the subject's Normal Stability can be performed and included in a data report.

The above tests, and other tests performable by the disclosed system, have multiple applications. Following is a nonexclusive group of application examples.

By measuring up to all degrees of freedom or the force components to calculate the center of pressure, this device and system has multiple applications in the biomechanical and medical fields; including, but not limited to, the measuring and testing of a subject's balance, coordination, gait, movement, posture, stability and instability, and sway. Generally, versions of this invention will be used to test for the existence of balance problems in a subject or the likelihood of a balance problem, as well as the magnitude of the problem, and aid in the determination of the cause; whether the cause is inner ear, muscular, neurological, ocular, skeletal related, or otherwise. The disclosed plate such as 20 is sensitive enough to measure the tremor(s) in patients, then using an algorithm, the data collected is viewed in the frequency domain to reveal the potential ability to decipher such things as the stage of Multiple Sclerosis, and the efficacy of drug dosages for Parkinson's disease.

There are many applications beyond the general-clinical measuring and testing. For example, this device and system can measure and test for the effects and impairments of drugs (e.g., alcohol) on a subject's capability to function. Likewise, this system can be employed to measure an athlete's functional capability prior to, during, or after activity, or to measure the subject's capability to return to the activity after an injury.

Therefore, the presently disclosed balance analysis system improves upon the prior art and provides for the means of measuring and testing a subject's balance neither contemplated nor demonstrated by the prior art.

We claim:

1. An apparatus for making a balance measurement, a center of pressure measurement, and a tremor measurement of a subject comprising, in combination;

a) a generally horizontally disposed platform configured to receive a subject standing upon and applying forces and moments to said platform;

b) a pair of spaced beams extending substantially parallel to said platform and connected to said platform to support said platform upon a generally horizontally disposed substrate, each of said beams including a top and bottom surface, said bottom surface provided with a central portion and opposing end portions, said central portion configured to engage said substrate in a force-transmitting relationship and each of said end portions raised above said substrate in non-force-transmitting relationship to said substrate to form a cantilever relative to said central portion of said beam;

c) at least one strain gage operatively attached to a respective one of said end portions of said beams; and d) data collection, measuring and transmission apparatus operatively connected to said strain gages to convert a signal from said strain gages to data representing forces and moments applied to said platform by said subject.

2. The apparatus defined in claim 1 further including a pad of compressible material overlying at least a portion of the top surface of said platform in force transmitting relationship to receive a subject standing upon said platform.

3. The apparatus defined in claim 1 further including a plurality of strain gages mounted to a respective one of each of said end portions of said beams.

* * * * *